(12) United States Patent
Meles

(10) Patent No.: US 10,578,527 B2
(45) Date of Patent: Mar. 3, 2020

(54) TEST SYSTEM COMPRISING A HEATING DEVICE AND METHOD FOR IMPLEMENTING A TEST SYSTEM

(71) Applicant: CHOPIN TECHNOLOGIES, Villeneuve-la-Garenne (FR)

(72) Inventor: Jean-Pierre Meles, Drancy (FR)

(73) Assignee: CHOPIN TECHNOLOGIES, Villeneuve la Garenne (FR)

( * ) Notice: Subject to any disclaimer, the term of this patent is extended or adjusted under 35 U.S.C. 154(b) by 239 days.

(21) Appl. No.: 15/558,722

(22) PCT Filed: Mar. 14, 2016

(86) PCT No.: PCT/FR2016/050563
§ 371 (c)(1),
(2) Date: Sep. 15, 2017

(87) PCT Pub. No.: WO2016/146928
PCT Pub. Date: Sep. 22, 2016

(65) Prior Publication Data
US 2018/0073966 A1 Mar. 15, 2018

(30) Foreign Application Priority Data

Mar. 16, 2015 (FR) .................................. 15 52101

(51) Int. Cl.
*G01N 1/44* (2006.01)
*H05B 6/10* (2006.01)
(Continued)

(52) U.S. Cl.
CPC .............. *G01N 1/44* (2013.01); *B01L 3/5082* (2013.01); *B01L 7/00* (2013.01); *G01N 11/12* (2013.01);
(Continued)

(58) Field of Classification Search
CPC .. G01N 1/44; G01N 11/12; B01L 7/00; B01L 3/5082; B01L 2300/1816; B01L 2300/0832; H05B 6/108
See application file for complete search history.

(56) References Cited

U.S. PATENT DOCUMENTS 2,930,098 A * 3/1960 Reimer ................... H01L 21/00
65/17.6
3,684,455 A * 8/1972 Smith ................... B01L 3/5082
422/413
(Continued)

FOREIGN PATENT DOCUMENTS

DE 1598437 A1 12/1970
EP 2709079 A1 3/2014
(Continued)

OTHER PUBLICATIONS

English machine translation for JP 2007-076201.*
International Search Report related to Application No. PCT/FR2016/050563 reported dated Jun. 16, 2016.

*Primary Examiner* — Daniel S Larkin
*Assistant Examiner* — Anthony W Megna Fuentes
(74) *Attorney, Agent, or Firm* — Miller Matthias & Hull LLP

(57) ABSTRACT

A test system comprising a heating device for heating content comprising a mixture of a first and a second product, said device comprising a test container suitable for receiving the content, a receiving container suitable for receiving the test container, a coil comprising induction turns, and a current source suitable for supplying current to the induction turns. The heating device is such that the induction turns are attached to the receiving container and extend helically concentrically around the receiving container. The test system further comprises an arm for mixing the content of the (Continued)

test container and a mechanism for guiding the arm. A method for implementing such a test system.

20 Claims, 6 Drawing Sheets

(51) Int. Cl.
   *B01L 3/00* (2006.01)
   *B01L 7/00* (2006.01)
   *G01N 11/12* (2006.01)
(52) U.S. Cl.
   CPC ...... *H05B 6/108* (2013.01); *B01L 2300/0832* (2013.01); *B01L 2300/1816* (2013.01)

(56) References Cited

U.S. PATENT DOCUMENTS

| | | | | |
|---|---|---|---|---|
| 4,283,703 A | * | 8/1981 | Horwitt | G01N 33/0016 204/421 |
| 4,329,136 A | * | 5/1982 | Willay | G01N 23/2202 425/174.8 R |
| 4,401,625 A | * | 8/1983 | Willay | G01N 1/44 422/240 |
| 5,201,797 A | | 4/1993 | Weng | |
| 5,412,185 A | * | 5/1995 | Sturman, Jr. | B01J 3/04 219/602 |
| 5,659,874 A | * | 8/1997 | Rault | B01J 19/126 219/429 |
| 5,686,006 A | * | 11/1997 | Gaspard | H05B 6/1254 219/622 |
| 6,599,484 B1 | * | 7/2003 | Zigler | G01N 35/1079 422/129 |
| 6,930,292 B1 | * | 8/2005 | Winther | B01L 3/50851 156/345.38 |
| 8,122,956 B2 | * | 2/2012 | Shammai | B01F 7/0005 166/100 |
| 8,616,118 B1 | * | 12/2013 | Lassota | A47J 31/446 99/299 |
| 2003/0121878 A1 | * | 7/2003 | Finneran | B01L 3/5082 215/247 |
| 2014/0197158 A1 | * | 7/2014 | Ijuin | G07F 11/70 219/628 |

FOREIGN PATENT DOCUMENTS

| | | |
|---|---|---|
| FR | 2726963 A1 | 5/1996 |
| JP | 2007-076201 * | 3/2007 |
| WO | WO 9902965 A1 | 1/1999 |
| WO | WO 2007124008 A2 | 1/2007 |

* cited by examiner

TEST SYSTEM COMPRISING A HEATING DEVICE AND METHOD FOR IMPLEMENTING A TEST SYSTEM

CROSS-REFERENCE TO RELATED APPLICATION

This Application is a 35 USC § 371 US National Stan filing of International Application No, PCT/FR2016/050563 filed on Mar. 14, 2016, and claims priority under the Paris Convention to French Application No. 15 52101 filed on Mar. 16, 2015.

FIELD OF THE DISCLOSURE

The invention relates to the technical field of test systems suitable for testing content. The test system comprises a device for heating content comprising a mixture of a first and a second product. In particular, the invention relates to the technical field of test systems comprising a device for heating content in order to conduct a test on the content, and methods for implementing such test systems. For example, the first product is a material in powder form prior to mixing, and the second product is a liquid product. The mixture is thus a suspension or solution of the first product which may be flour for example, and of the second product which may be an aqueous solution for example.

BACKGROUND OF THE DISCLOSURE

Sample testing comprising at least one heating step is in widespread use in many fields of application. For example, in order to measure and determine flour quality for the purposes of classification, it is common to do a test called the Falling Number test, which consists of testing a mixture of flour and liquid. A heating step is necessary for this test. Documents WO9902965 and DE1598437 present implementations of this test or similar tests. The Falling Number test is still used in practice, by placing the content in a rigid test container and placing the test container in a water bath in order to heat the content. The principle of a water bath means that water is consumed. Also, it is sometimes difficult to control the temperature of the content when using a water bath. This principle is also very resistant to temperature increases and to cooling. As the temperature of the bath depends on the altitude at which the test is performed, it is sometimes necessary to correct the values obtained by the test. Moreover, the manipulators using the bath to conduct the test must take significant safety precautions, particularly to prevent burns. Finally, the use of a water bath means that the test device has a large footprint.

In fields of application other than flour quality tests, various solutions are known from the prior art for implementing a test system comprising a heating device, in particular for testing content.

Document U.S. Pat. No. 2,930,098A discloses a quartz test container in two parts, received in an outer container made of quartz. Around the quartz outer tube, a mechanism with an endless screw guides a translationally mobile carriage supporting a coil extending in part around the quartz outer tube and heating the interior of the quartz tube, in particular by induction. This type of system has significant bulk and does not permit simple homogeneous heating of the test container content while avoiding temperature spikes at certain locations.

Document U.S. Pat. No. 3,435,170A aims to provide a solution for rapidly heating the content of a plurality of test containers. The test rack disclosed in this document comprises means for creating a magnetic field adapted to pass through the test rack so as to induce an electric current therein and heat the all the test containers on a regular basis. The system described, apart from its size as it is intended for testing several containers at once, permits an even heating of all the test containers, but does not ensure uniform heating of all the content of a test container.

Document EP0439900A2 relates to an induction heating furnace comprising a refractory crucible and a continuous metallic shell. Lugs may be installed on the shell, which permit translational movement of the furnace vessel into or out of the interior of the induction coil. The system described in document EP0439900A2 does not provide easy access to the heated content. In addition, the translational movement of the furnace vessel involves the use of a bulky moving device and special precautions for manipulation of the furnace.

Thus, the systems described in documents U.S. Pat. Nos. 2,930,098A, 3,435,170A, and EP0439900A2 appear to provide heating in which it is possible to control (at least partially) the temperature of the content to be heated, but all have numerous drawbacks, and in particular a large footprint, a complicated implementation of the device, significant usage precautions in order to avoid accidents, and/or are not easily adapted to heating content for the purposes of conducting a test.

There is therefore a need to create a test system comprising a heating device that is simple to implement and to manipulate without risk to operator safety and that has a small footprint while providing uniform heating of the content of a container for the purposes of conducting a test on said content.

SUMMARY OF THE DISCLOSURE

To this end, the test system according to the invention is a test system adapted for conducting tests on content, comprising a heating device for heating content comprising a mixture of a first and a second product, said device comprising:
- a test container suitable for receiving the content, the test container comprising a rigid hollow body defining an inner space and extending longitudinally along a container axis between a first end and a second end, the second end being closed, the test container comprising an inner surface defining the inner space and an outer surface opposite the inner surface,
- a receiving container suitable for receiving the test container, the receiving container comprising an inner surface oriented towards the outer surface of the test container and an outer surface opposite the inner surface,
- a coil comprising induction turns, and
- a source of current suitable for supplying current to the induction turns, the test system being characterized in that the induction turns are fixed to the receiving container and extend helically and concentrically around the receiving container, and in that said test system comprises an arm for mixing the content of the test container and a mechanism for guiding the arm within the inner space of the test container along the container axis, in a first direction and in a second direction that is opposite the first direction.

With these arrangements, homogeneous heating of the content of the test container is achieved, which allows conducting a quality test. Temperature spikes are avoided, as is the possible formation of crusted content in the test container near the test container walls. Induction heating allows controlling the temperature of the content and the kinetics of heating the content. The presence of the receiving container makes it possible to place the induction turns in position, and multiple tests can be successively performed without long periods of latency between tests. The arm and the guide mechanism for the arm make it possible to mix the content of the container autonomously, with no need for outside intervention. Finally, the test system thus implemented has a small footprint. Induction heating thus offers many advantages, particularly in comparison to other heating methods which could also be (and have been) considered by the applicant, for example such as heating with a heating resistor, heating with infrared radiation, heating in an oven, or heating by microwave. Heating a test container with a heating resistor turns out to take a particularly long time and does not provide complete control of the temperature of the content. Heating a test container containing content comprising a mixture of a first and a second product in an oven raises the issue of implementing an enclosure, which results in a large footprint, and the need to monitor numerous parameters of the enclosure which are onerous to implement, unlike induction heating. Finally, heating by microwave does not achieve satisfactory heating of content comprising a powder and a liquid for the purpose of conducting tests, in particular Falling Number tests, again unlike induction heating.

In one embodiment, the heating device further comprises an intermediate container arranged between the receiving container and the test container, the intermediate container being suitable for receiving the test container and being suitable for being received in the receiving container, the intermediate container comprising an inner surface oriented towards the outer surface of the test container and an outer surface opposite the inner surface and oriented towards the inner surface of the receiving container.

In one embodiment, the intermediate container is made of a magnetic material or contains a magnetic material. For example, the intermediate container is made of soft iron or mild steel.

In one embodiment, the intermediate container is fixed in the receiving container.

In one embodiment, the intermediate container and the receiving container are combined.

In one embodiment, the test container is movable relative to the intermediate container.

In one embodiment, the receiving container comprises a plurality of bosses arranged on the inner face of the receiving container, the plurality of bosses being adapted for centering and fixing the intermediate container in the receiving container.

In one embodiment, the test container has an insulating handle.

In one embodiment, the insulating handle is arranged near the first end of the test container. The handle thus facilitates the gripping of the test container by an operator, in particular after testing the content and heating the content of the test container.

In one embodiment, the first end of the test container defines a filling opening.

In one embodiment, the second end of the test container has a draining opening closed by a cap. The presence of the cap allows opening the test container on both sides, in particular to facilitate cleaning said container. For example, the second end has a thread and the cap is screwed onto the second end. A seal may be provided to seal the test container near its second end.

In one embodiment, the receiving container comprises a continuous helical groove. The helical groove extends over the outer surface of the receiving container.

In one embodiment, the induction turns of the coil are accommodated in the groove. The groove thus guides and retains the induction turns in position on the receiving container. The induction turns are thus fixed on the outer surface of the receiving container in a manner that winds around it. The groove prevents any displacement of the induction turns.

In one embodiment, the receiving container comprises a base and the second end of the test container or an end of the intermediate container is suitable for resting on the base.

In one embodiment, the bosses ensure that the intermediate container is retained in the receiving container.

In one embodiment, the test container comprises a material of low friction coefficient, such as glass, aluminum, etc. For example, the test container is made entirely of aluminum. Such a material ensures the durability of the test container and eliminates any chemical interaction with the content of the test container while enabling proper heating of the content.

In one embodiment, the receiving container is made by sintering, in particular by sintering powder. For example, the receiving container is formed using a three-dimensional printer. In such case, the receiving container can be formed by printing in three dimensions with sintered powder. In addition, the groove if applicable can be formed directly when printing the receiving container and does not have to be subsequently machined in a second step. This receiving container may be associated with a second casing which in this case acts as the receiving container.

In one embodiment, the arm extends longitudinally along an arm axis between a first end and a second end, the first end being suitable for being arranged in the inner space of the test container, the second end being suitable for being retained outside the inner space of the test container.

In one embodiment, the guide mechanism is arranged facing the filling opening and comprises a releasable arm retention device. As the retention device is releasable, it can therefore retain the arm in a first mode and disengage from the arm in a second mode.

In one embodiment, additionally the retention system comprises an electromagnet and the arm comprises a magnetic element. Thus, for example, when power is supplied to the electromagnet the arm is retained on the guide mechanism, and when power is no longer supplied the arm is independent (or disengaged) from the guide mechanism. The electromagnet ensures actuation precision, limits play, and prevents impacts during guidance of the arm, in particular when changing directions. The retention system may comprise a suction cup as an addition or an alternative to the electromagnet.

In one embodiment, additionally the magnetic element (or a magnet) is fixed to the second end of the arm.

In one embodiment, the test system further comprises a force sensor suitable for measuring a thrust, penetration, or retention force of the arm.

In one embodiment, the electromagnet is fixed to the force sensor.

In one embodiment, the test system further comprises:
  an inner housing, in which are arranged the receiving container, the test container, and where appropriate the intermediate container, an outer housing, the inner housing being received within the outer housing, and an insulating material, arranged between the outer housing and the inner housing.

With these arrangements, the heating device can be used safely and with no risk of burning the user, the insulating material providing insulation of the outer housing serving as an outer casing for the heating device. The test container is movable and can be inserted and removed from the receiving container or intermediate container.

In one embodiment, the test system further comprises a frame on which the guide mechanism is fixed, the outer housing being fixed to the frame so as to be pivotally movable about a tilt axis. This arrangement allows easy installation and removal of the test container into and from the intermediate container or receiving container.

In one embodiment, the test system further comprises a ventilation device suitable for cooling the test container. For example, the ventilation device comprises one or more ventilation risers. The ventilation device may comprise, additionally or alternatively, a fan suitable for cooling the test container. The fan may possibly be coupled to Peltier elements.

In one embodiment, the inner housing comprises an insulating material, for example polyvinylchloride.

In one embodiment, the test system comprises a temperature sensor suitable for measuring the temperature of the content of the test container.

In one embodiment, the temperature sensor is a thermocouple or equivalent suitable for coming into contact with the outer surface of the receiving container, intermediate container, and/or test container.

In one alternative embodiment, the temperature sensor comprises an infrared sensor, for example contactless, measuring the surface temperature of the test container. In one embodiment, the temperature sensor measures the temperature of the inner surface of the intermediate container.

According to another aspect, an object of the invention may be a method for implementing a test system as described, comprising the steps of:

supplying power to the induction turns so as to create induced eddy currents and to heat by induction the inner space defined by the intermediate container, filling the test container with content comprising a first and a second product, for example a material in powder form and a liquid product, placing the test container inside the intermediate container, mixing the content of the test container with the arm connected to the guide mechanism, by moving the arm along the direction of the container axis in the first direction and in the second direction, supplying power to the induction turns so as to create induced currents and heat by induction the content of the test container and/or the inner space defined by the intermediate container.

In one embodiment, additionally the method further comprises the steps of:

releasing the arm from the retention device so that the arm drops into the test container, measuring the time it takes the arm to drop into the test container.

In one embodiment, additionally the method further comprises the steps of:

providing a temperature sensor, monitoring the temperature of the outer surface of the test container, and thus of the content.

In an additional and/or alternative embodiment, the method further comprises the steps of:

providing a force sensor, measuring the force exerted by the arm when mixing the content of the test container with the arm and/or after its release by the retention device, and/or measuring the thrust, penetration, and/or retention force exerted by the arm.

Thus, the described method and/or the described heating device makes it possible to carry out the Falling Number test described above with its determination of enzyme activity, but also other tests for determining flour properties such as rheological properties for example, or tests for determining properties of the starch portion of the flour. The device described also allows combining multiple tests, which has not previously been possible in conventionally used devices.

The figures in the drawings are now briefly described.

The following is a detailed discussion of several embodiments of the invention, accompanied by examples and references to the drawings.

DETAILED DESCRIPTION OF THE DISCLOSURE

Figure 1:
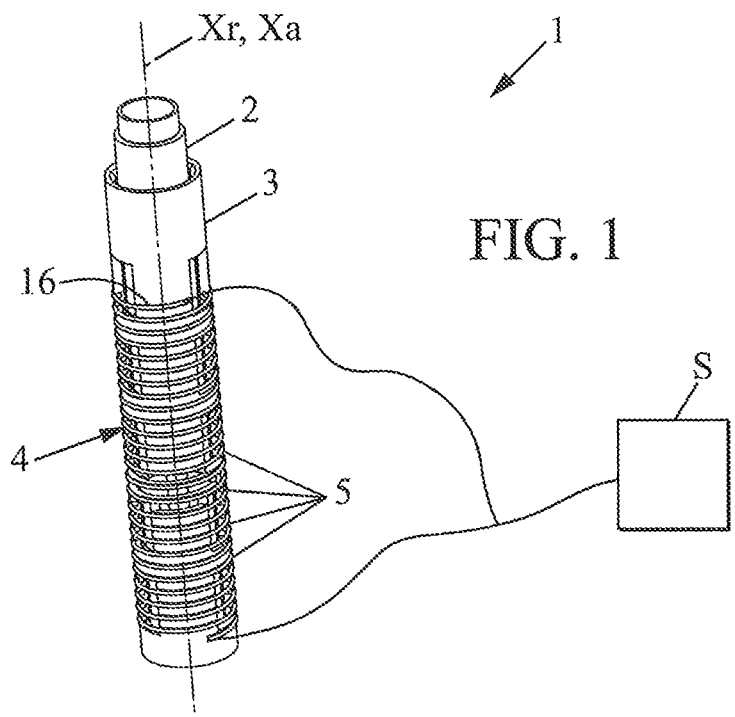
FIG. 1 is an isometric view of a first alternative embodiment of a device for heating a test system according to the invention, the heating device comprising a test container and a receiving container, on which a coil with induction turns is provided.

FIG. 1 illustrates a heating device 1 of a test system 17. The heating device 1 is a device for heating content, in particular content comprising a mixture of a first and a second product. Before mixing, the first product may be a material in powder form and the second product a liquid product. The heating device 1 comprises in particular, as visible in FIG. 1, a test container 2, a receiving container 3, a coil 4 comprising induction turns 5, and a source of current S adapted to supply power to the induction turns 5. The test container 2 is intended for receiving content, in particular for the purposes of conducting a test on the heated content.

Figure 2:
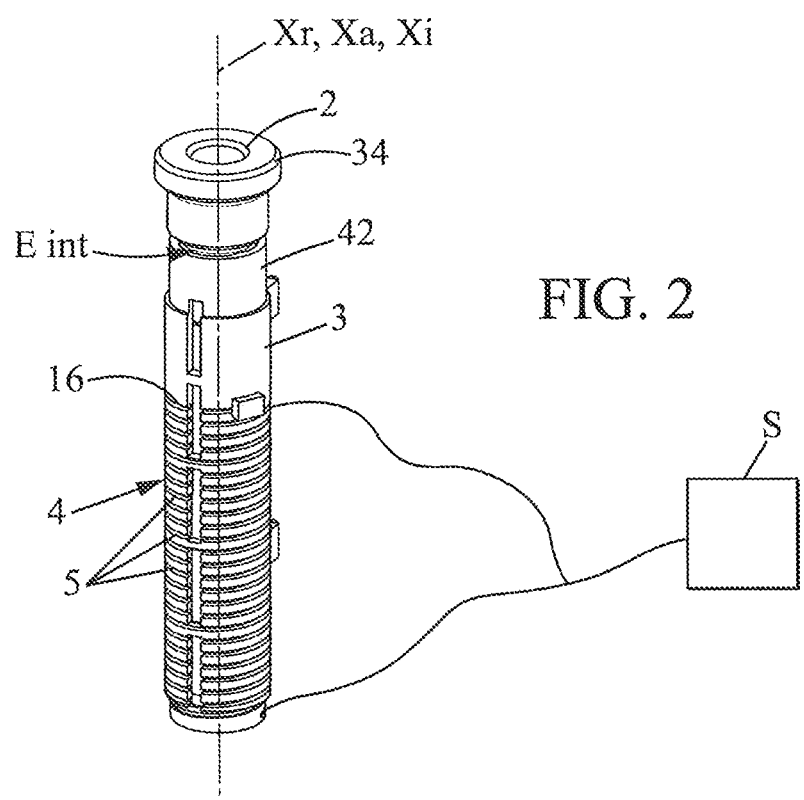
FIG. 2 is an isometric view of a second alternative embodiment of a device for heating a test system according to the invention, the heating device comprising a test container, an intermediate container, and a receiving container, on which a coil with induction turns is provided.

Preferably, and as illustrated in FIG. 2, the heating device 1 further comprises an intermediate container 42 arranged between the test container 2 and the receiving container 3.

Figure 4:
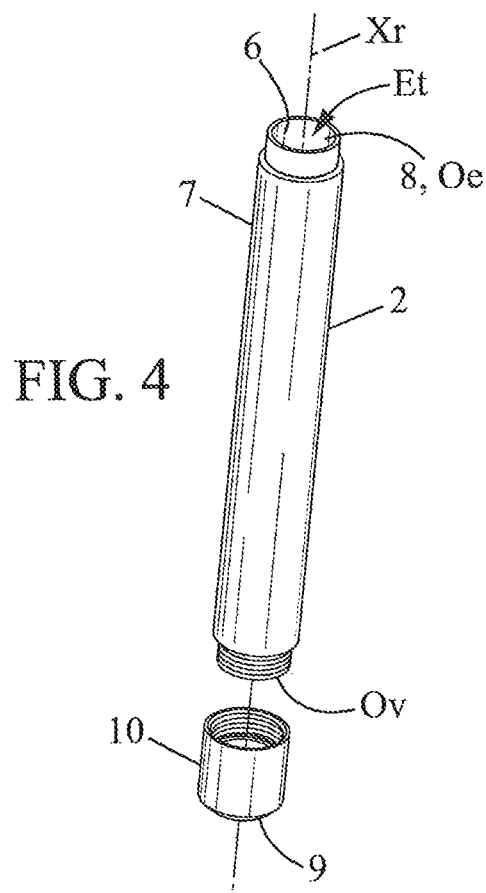
FIG. 4 is an isometric view of a test container comprising a first and a second end, the second end being provided with a cap.
Figure 5:
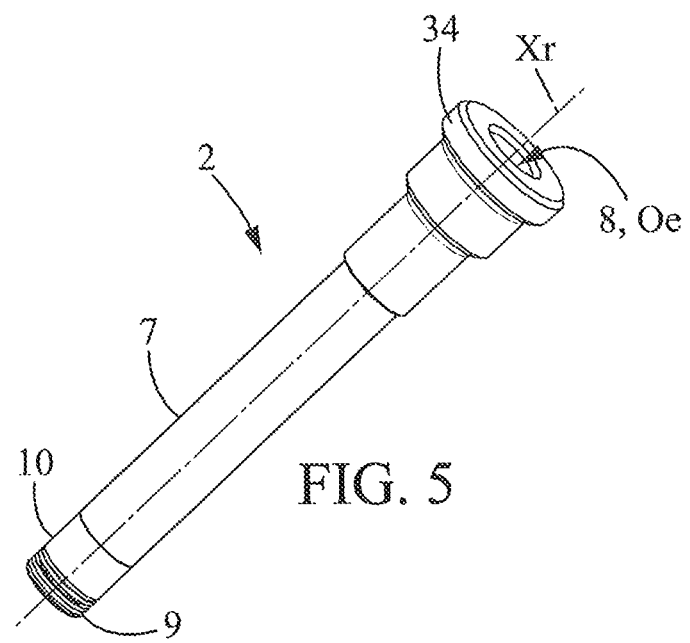
FIG. 5 is an isometric view of a test container according to an alternative embodiment comprising a first and a second end, the second end being provided with a cap and the first end being provided with a handle, in particular an insulating handle.

As shown in FIG. 1, 2, or in more detail in FIGS. 4 and 5, the test container 2 has a cylindrical shape. The test container 2 is for example a test tube type of container and comprises a rigid hollow body defining an inner space and extending longitudinally along a container axis Xr. The test container 2 has an inner surface 6, this inner surface 6 defining the inner space Et. The test container 2 also comprises an outer surface 7, opposite to the inner surface 6. The test container 2 may have a capacity of less than one liter. The test container 2 may have the shape and capacity of a test tube.

As can be seen in FIGS. 4 and 5, the test container 2 extends along the container axis Xr between a first and a second end 8, 9. For example, the first end 8 of the test container 2 defines a filling opening Oe. In particular, the inner space Et of the test container 2 can receive content through the filling opening Oe. The second end 9 of the test container 2 can also define an opening Ov, for example a draining opening Ov. The draining opening Ov can be closed by a cap 10. For example, the second end 9 of the test container 2 comprises a thread and the cap 10 is screwed onto the thread. Such a draining opening Ov and such a cap 10 enable in particular the effective cleaning of the test container 2. A seal (not shown) may be provided between the cap 10 and the hollow body of the test container 2, to ensure fluidtightness of the test container 2, in particular as it is filled with content. However, in an alternative embodiment, the test container 2 may have a closed second end 9 without a removable cap 10.

In the alternative embodiment shown in particular in FIG. 2, the test container 2 is made of a material enabling good heat transfer. In addition, the material of the test container has a low coefficient of friction. The test container 2 is also made of a light material. For example, the test container 2 is made of aluminum. However, other materials can be considered, in particular those having a good heat transfer coefficient. The cap 10 is for example made of a material similar to the material of the rigid hollow body. In the alternative embodiment of FIG. 1 (meaning the embodiment without an intermediate container), the test container is preferably of magnetic material.

The test container 2 is intended to be housed in the receiving container 3. The test container may be housed directly in the receiving container 3, as shown in FIG. 1 or, in a preferred alternative of the invention illustrated in FIG. 2, it may be housed in the intermediate container 42 which itself is housed in the receiving container 3.

Figure 3:
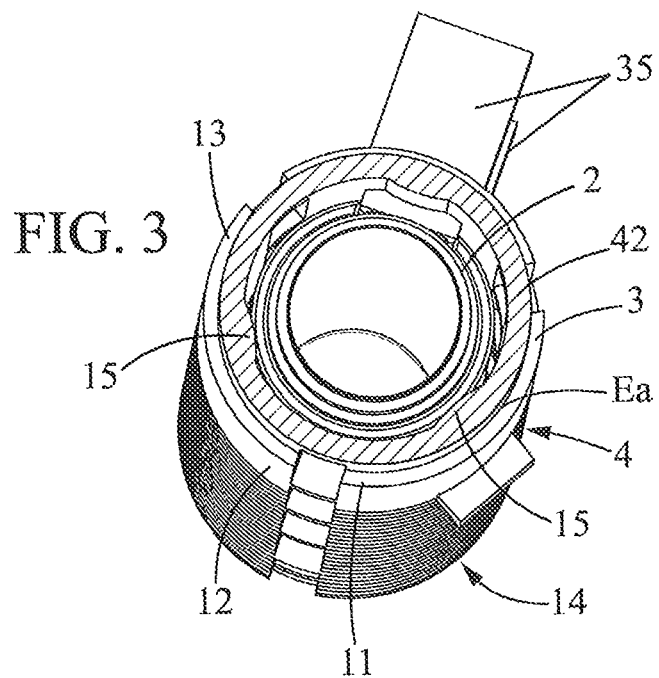
FIG. 3 is a top view of the intermediate and receiving containers of FIG. 2.

For example, as can be seen in FIGS. 2 and 3, the intermediate container 42 is arranged between the receiving container 3 and the test container 2. The intermediate container 42 is adapted to receive the test container 2 and to be received within the receiving container 3. The intermediate container 42 has an inner surface oriented towards the outer surface of the test container 2 and an outer surface opposite to the inner surface. The intermediate container 42 may be cylindrical in shape. The intermediate container 42 defines an inner space Eint and the test container is intended to be positioned in the inner space of the intermediate container 42. In particular, the intermediate container has an inside diameter greater than the outside diameter of the test container 2. Furthermore, the intermediate container 42 has a length substantially equal to that of the test container 2. The intermediate container 42 extends longitudinally along an intermediate axis Xi between a first end and a second end. The first end defines an opening through which the test container 2 can be inserted and/or removed, for example before and/or after conducting a test with the test system 17. The base of the intermediate container 42 acts as a stop for the test container 2 along the intermediate axis Xi.

The intermediate container 42 comprises or is made of a magnetic material. In such case, the intermediate container 42 comprises a material having good magnetic characteristics. The material also has a good heat transfer coefficient and good resistance and high magnetic permeability. For example, the intermediate container 42 comprises or is made of a material such as soft iron or mild steel.

The intermediate container may be inserted by force into the receiving container 3 and may be mounted so as to be fixed relative to the receiving container 3.

The receiving container 3 is, as represented in FIGS. 1, 2, 3, of cylindrical shape.

The receiving container 3 comprises a hollow body defining an inner space Ea (visible in FIG. 3) which is intended to house the intermediate container 42 (as visible in FIG. 2) or the test container 2 (as visible in FIG. 1).

For example, the receiving container 3 comprises a base and the second end 9 of the test container 2 or intermediate container 42 is adapted to be facing the base. The receiving container 3 comprises an inner surface 11 which defines its inner space Ea and an outer surface 12 opposite the inner surface. The inner surface 11 of the receiving container 3 is facing the outer surface of the intermediate container 42. In particular, the receiving container 3 can have an inside diameter greater than the outside diameter of the intermediate container 42. Moreover, the container 3 has a length substantially equal to that of the test container 2 and of the intermediate container 42. The receiving container 3 extends longitudinally along a receiving axis Xa between a first end 13 and a second end 14. The first end 13 defines an opening through which the intermediate container 42 is inserted for example. In such case, the intermediate container is fixed to the receiving container 3 so that the intermediate container is not movable relative to the receiving container.

The receiving container 3, and more specifically the inner face 11 of the receiving container 3, may comprise a device 15 for centering the intermediate container 42. For example, a series of bosses 15 may be provided on the inner face of the receiving container 3. The bosses 15 may extend over the entire length of the receiving container 3 and/or over a portion of the receiving container 3. For example, three bosses may be provided at equal intervals around the circumference of the inner surface 11 of the receiving container 3. The bosses 15 fix and center the intermediate container 42 within the receiving container 3. The plurality of bosses may also allow the possibility of air circulation around the intermediate container. In an alternative embodiment, the intermediate container 42 may also comprise a device for centering the test container. For example, a series of bosses may be distributed around the circumference of the inner surface of the intermediate container 42.

The coil 4 comprising induction turns 5 is fixed to the receiving container 3. More specifically, the coil 4 extends helically and concentrically around the receiving container 3. For example, the coil 4 is fixed to the outer surface 12 of the receiving container 3. In an alternative embodiment, the coil may be directly fixed to the intermediate container 42. In this embodiment, the intermediate container and the receiving container form a single container.

The receiving container 3 may be formed by sintering, in particular by sintering powder. In such case, the receiving container 3 may be formed using a three-dimensional printer. For example, the receiving container 3 may be formed by printing in three dimensions with sintered powder. When creating the receiving container 3, it is possible to provide a helical groove 16 on the outer face 12 of the receiving container 3. The helical groove 16 may be formed directly during production of the receiving container 3 by the three-dimensional printer, in the same production step. However, in an alternative embodiment, the groove 16 may be formed by machining the outer surface 12 of the receiving container 3.

In such case, the helical groove 16 is adapted to receive the turns of the coil 4. Specifically, the turns of the coil 4 are secured in the helical groove 18. Thus, the induction turns 5 of the coil 4 are immovable relative to the receiving container 3.

The groove 16 may have dimensions that are substantially equal to, even slightly larger than, those of the induction turns 5 of the coil 4. The groove 16 and/or the induction turns 5 of the coil 4 may extend in a spiral over the entire length of the receiving container 3 or over a portion greater than or equal to 50% of the length of the receiving container 3, for example over a portion greater than or equal to 70% of the length of the receiving container 3.

The induction turns 5 of the coil 4 may be uniformly distributed over the outer surface 12 of the receiving container 3. For example, the coil 4 has twenty-six induction turns 5 equally distributed in a spiral over the outer surface of the receiving container 3. In alternative embodiments, the coil 4 may comprise more or less than twenty-six induction turns. The induction turns 5 may be centered along the receiving axis Xa, such that the first and second ends 13, 14 of the receiving container 3 are devoid of induction turns 5. The spacing between the turns of the coil 4 may be regular, or conversely may be dependent on the position of the turn along the receiving axis Xa.

In the present case the coil 4 is made of Litz wire. Litz wire is more effective than copper wire. However, in an alternative embodiment, the coil 4 may be made of copper wire and the Joule heating from the copper can be used in the heating device 1.

The source of current S allows supplying power to the coil 4 and thus to the induction turns 5, enabling induction heating. In such case, when the test container 2 or the intermediate container 42 is housed in the receiving container 3, the intermediate container 42 (or test container 2 in the variant shown in FIG. 1) will be bathed in an electromagnetic field created by the induction turns 5 and the material having high magnetic permeability of the intermediate container 42. Eddy currents will then be generated and the energy will dissipate as heat in the intermediate container. Induction heating of the intermediate container and of the inner space Eint of the intermediate container is thus ensured. When the test container 2 is arranged within the inner space Eint of the intermediate container 42, this test container 2 and its content are heated.

Figure 9:
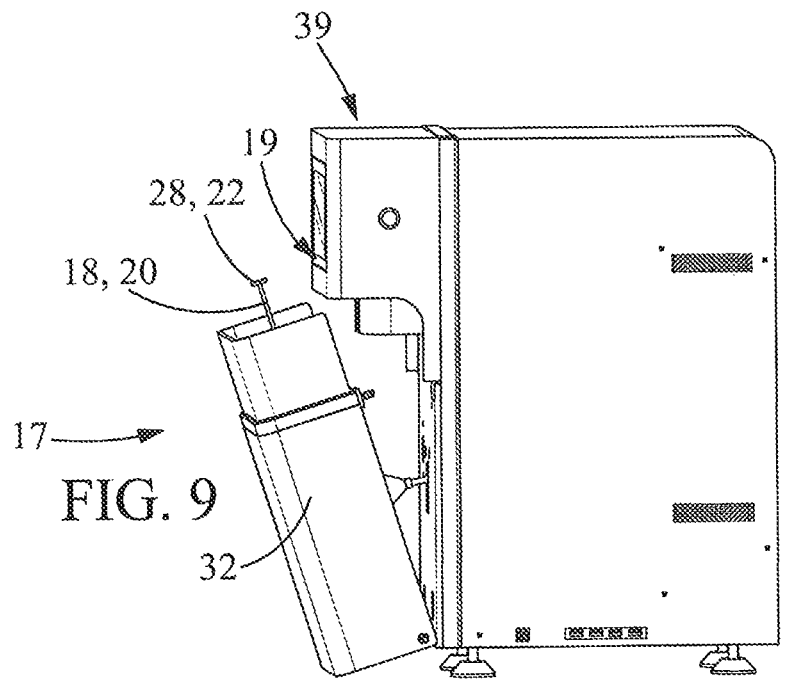
FIG. 9 shows a side view of the test system according to the invention in a first arrangement with a frame and with measurement and control means, and where the outer housing of FIG. 7 is tilted relative to the frame to allow withdrawal or insertion of the test container before or after a test on the content of the test container.
Figure 10:
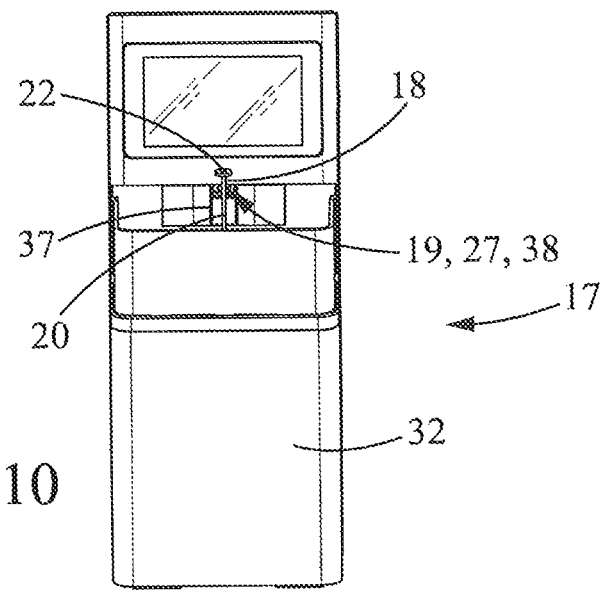
FIG. 10 shows a front view of the test system of FIG. 9.
Figure 11:
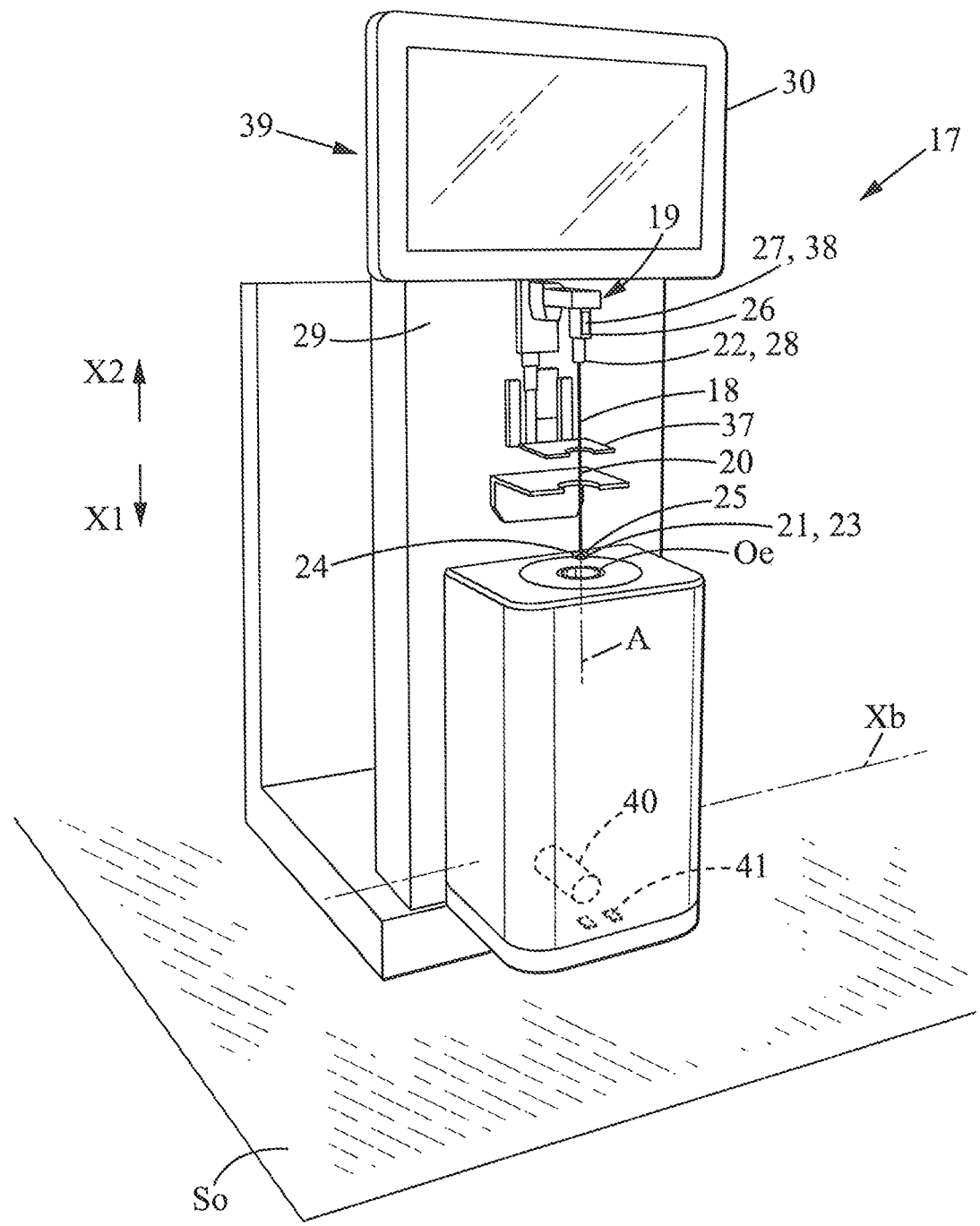
FIG. 11 schematically represents an isometric view of a test system according to the invention, with the outer housing in which are arranged the test container, the intermediate container, and the receiving container, and the measurement and control means, and the outer housing being arranged to enable conducting a test on the content of the test container.

The heating device 1 described can be integrated into the test system 17 suitable for conducting tests on content, as shown in particular in FIGS. 9 to 11.

The test system 17 further comprises an arm 18 and a mechanism 19 for guiding the arm 18.

The arm 18 is suitable for mixing the content of the test container 2. For example, the arm 18 comprises a rod extending longitudinally along an arm 18 axis between a first and a second end 21, 22.

For example, the first end is adapted for insertion into the inner space Et of the test container 2, in particular for mixing and/or homogenizing the content of the test container 2. When the arm 18, or at least the first end 21 of the arm 18, is inserted into the test container 2, the arm 18 axis is substantially aligned with the container axis Xr.

In such case, the second end 22 of the arm 18 is adapted to be arranged outside the test container 2.

The first end 21 may comprise a mixing member 23 of substantially circular shape extending in a plane normal to the arm axis A. As the first end 21 of the arm 18 is to be introduced into the test container 2, the mixing member 23 has dimensions that are therefore substantially equal or smaller than those of the hollow body of the test container 2.

In particular, the mixing member 23 may have a diameter equal or slightly smaller than the inside diameter of the test container 2. The mixing member 23 may be provided with openings to allow mixing the content of the test container 2. For example, the mixing member 23 has a substantially circular outer ring 24 which is connected to the rod by three fastening lugs uniformly distributed around the rod 20.

The arm 18 is driven by the guide mechanism 19. The guide mechanism 19 guides the arm 18, and more particularly the first end of the arm 18, within the inner space of the test container 2 along the container axis Xr, in a first direction X1 and in a second direction X2 that is opposite the first direction X1. In the current case the guide mechanism 19 guides the arm 18 in translation so that the arm and in particular the mixing member 23 can move back and forth within the inner space of the container and thus can mix the content of the test container 2. In alternative embodiments, other types of guide kinematics could be implemented, such as rotational guidance for mixing the content of the test container 2.

The guide mechanism 19 may be an electric actuator with an actuation rod or it may comprise a wheel and reversible endless screw system. Other guide mechanisms suitable for transmitting translational movement in one direction then in another can be envisaged.

The arm 18 is connected to the guide mechanism 19 by a retention device 26. In such case the retention device 26 is releasable. Releasable is understood to mean that the retention device 26 may be in a restraining mode in which the arm 18 is mechanically connected to the guide mechanism 19, or in a free mode in which the arm 18 is no longer mechanically connected to the guide mechanism 19 (the arm is uncoupled from the guide mechanism).

For example, the retention device 26 comprises an electromagnet 27. The second end 22 of the arm 18 is provided with an element of magnetic material, for example a magnet 28, or comprises a magnetic material. In such case, the second end 22 of the arm 18 may have a flange made of a magnetic element. In such case, when the electromagnet 27 is receiving power, the retention device 26 is in said retaining mode and the guide mechanism 19 is mechanically connected to the arm 18 (by magnetic attraction). The guide mechanism 19 can therefore impart motion to the arm 18, in particular a back-and-forth motion so that the arm 18, and in particular the mixing member 23 of the arm 18, moves back and forth within the inner space of the test container 2, in the first direction X1 and in the second direction X2, and thus mixes the content of the test container 2. The path of the arm 18 in the test container 2 may for example be adjusted according to the length of the test container 2 and the amount of content present in the test container 2.

When the electromagnet 27 stops receiving power, the magnetic attraction disappears and the arm 18 is no longer connected or coupled to the guide mechanism 19.

In the embodiment shown in FIG. 11, in an assembled configuration (ready to conduct a test), the guide mechanism 19 and the retention device 26 are arranged above the filling opening Oe of the test container 2. In other words, the guide mechanism 19 and the retention device 26 are arranged facing or in line with the filling opening of the test container 2. The arm 18 can thus be aligned with the container axis Xr.

As shown in FIG. 11, the guide mechanism 19 is fixed to a frame 29 of the test system 17. The frame 29 of the test system 17 rests on a support So (which may be the floor or the mat of a table for example). The support So defines a plane.

The frame 29 may support an interface member 30 for the user of the test system 17, for entering various parameters for the test such as the frequency and/or the shaking time and/or for displaying the test results.

The heating device 1 is fixed to the frame 29 of the test system 17 as well.

Figure 6:
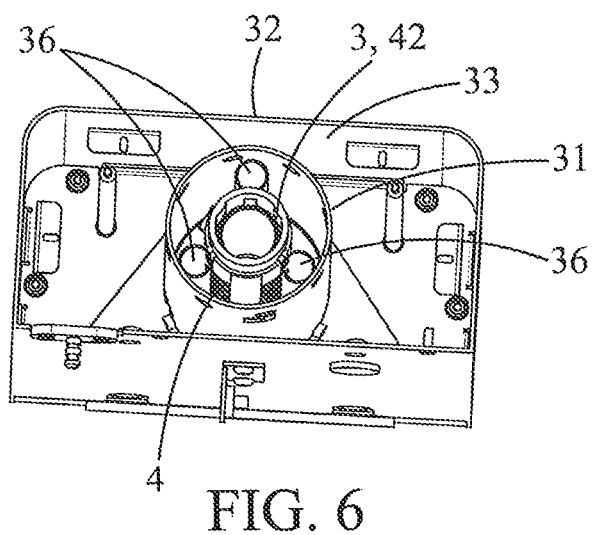
FIG. 6 represents a top view of the intermediate container and the receiving container within an inner housing, which is itself inserted into an outer housing.
Figure 7:
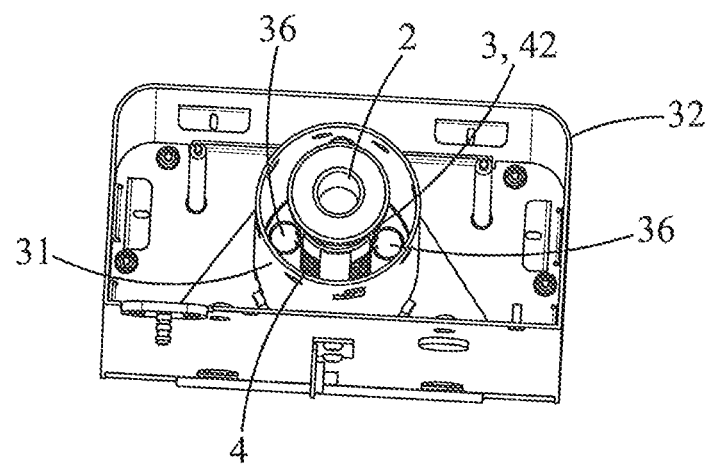
FIG. 7 shows the top view of FIG. 6 of the intermediate container and the receiving container within an inner housing, which is itself inserted into an outer housing, the test container being inserted into the intermediate container.
Figure 8:
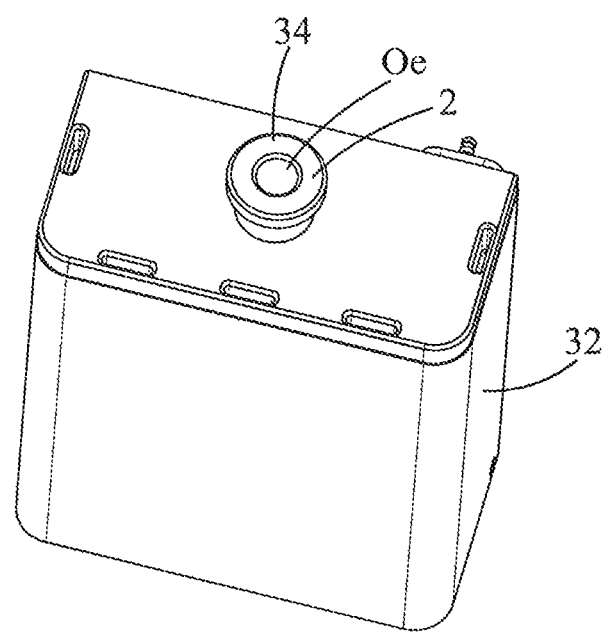
FIG. 8 shows an isometric view of the outer housing of the test system.

In the embodiment shown in FIGS. 6, 7, and 8, the test system 17 may comprise an inner housing 31 and outer housing 32.

The heating device 1 may be arranged in the inner housing 31. In particular, as shown in more detail in FIG. 6, the receiving container 3, the intermediate container 42, and the coil 4 are arranged within the inner housing 31. The test container 2, which is movable relative to the receiving 3 and intermediate 42 containers, is also movable relative to the inner housing 31. In FIG. 7, the test container 2 is in position in the intermediate container 42. The inner housing 31 may be cylindrical or substantially cylindrical in shape and define a hollow body in which are housed the receiving container 3 and the coil 4.

For example, the inner housing 31 comprises an insulating material, for example polyvinylchloride. The inner housing 31 may be made entirely of insulating material, for example polyvinylchloride. The dimensions of the inner housing 31 depend on the dimensions of the receiving container 3. In particular, in the case of an inner housing 31 of cylindrical shape, the inside diameter of the inner housing 31 is greater than the outside diameter of the receiving container 3. In particular, the induction turns 5 of the coil 4 will be at a distance from the inner surface of the inner housing 31.

The inner housing 31 is accommodated in the outer housing 32. The outer housing 32 may have a substantially parallelepiped shape as shown in FIGS. 6 and 7, or any other shape. The outer housing 32 has an inner face oriented towards the inner housing 31 and an outer face opposite the inner face. The outer housing 32 is in particular in direct contact with the user of the test system 17 in the current embodiment, the outer face of the outer housing 32 is visible to a user of the test system 17.

As represented in FIG. 8, the outer housing 32 comprises a lid and fully encloses the assembly composed of the receiving container 3, the intermediate container 42, the coil 4, and the inner housing 31, so that a user cannot access these elements without opening the lid of the outer housing 32. The outer housing 32 thus ensures the safety of a user of the test system 17. The lid of the outer housing in the current embodiment has a hole centered on the receiving axis Xa and which allows insertion and removal of the test container 2.

The coil 4, the receiving container 3, the intermediate container 42, and the inner housing 31 are fixed in the outer housing 32 such that they are not intended to move relative to the outer housing 32. The test container 2, which is movable relative to the receiving container 3 or intermediate container 42, is also movable relative to the outer housing 32.

An insulating material 33 may be arranged between the outer housing 32 and the inner housing 31. This insulating material 33 insulates the outer housing 32 and thus prevents any heating of the outer housing 32. For example, the insulating material 33 may be a thin multilayer insulation, possibly of the type ISO7 PRO®.

When the outer housing 32 is closed (as can be seen in FIG. 8), the test container 2 can be inserted into or removed from the intermediate container 42, even if the latter is not visible from the outside. It is therefore possible to clean the test container 2 or to fill the test container 2 without having to disassemble or open the outer housing 32. It is possible to manipulate the test container 2 independently of the receiving container 3, intermediate container, and/or inner housing 31 and/or outer housing 32. In the current embodiment the test container 2 may comprise a gripping flange 34 near its first end, to enable removal and insertion of the test container 2. For example, the gripping flange 34 extends around the entire periphery of the filling opening Oe. The gripping flange may comprise a bent portion or rim enabling a user to raise or remove the test container 2. The gripping flange 34 comprises a thermally insulating material for example. The gripping flange forms an insulating handle 34, shown in particular in FIG. 5. The handle may be insulating or made of an insulating material. In particular, the handle 34 gives the manipulator a more ergonomic and secure grip on the test container before or after conducting a test with the test system. In particular, after a test, the test container 2 may have a temperature close to 100° C. and the handle allows it to be handled without being burned.

In an operating state of the test system 17, the test container 2 is housed in the outer housing 32 and is centered in the intermediate container 42 and the receiving container 3. The outer housing 32 comprising the test container 2 and the guide mechanism 19 on which the arm 18 is mounted are arranged one above the other in a direction parallel—or substantially parallel—to the direction normal to the plane of the support So, such that the arm 18 is arranged in alignment with the filling opening of the test container 2.

To facilitate insertion and removal of the test container 2 into and from the outer housing 32, in particular so that the guide mechanism 19 and/or the arm 18 do not interfere with the insertion and removal of the test container 2 into and from the outer housing 32, the outer housing 32 is assembled to the frame 29 so as to be pivotable about a tilt axis Xb. Thus, the assembly consisting of the outer housing 32, the inner housing 31, the intermediate container 42, the receiving container 3, and the coil 4 can be pivoted relative to the frame 29 and therefore relative to the guide mechanism 19 which is fixed in a non-pivoting manner relative to the frame 29, in order to facilitate the insertion and removal of the test container 2 before and after a test, as can be seen in FIGS. 9 and 10.

The outer housing 32 may be locked (by a suction cup system, for example) to the frame 29 when the arm 18 is mixing the content or when the content is being heated. However, other systems for locking the position of the outer housing can be envisaged.

When the test system 17 is in the ready state, the receiving axis Xa and the intermediate axis Xi are aligned with the arm axis A. The suction cup system locks the position of the outer housing relative to the frame 29, to avoid any chance of pivoting.

In a state allowing the mounting of the test container 2 in the intermediate container 42 (and therefore in the receiving container 3), meaning when the outer housing 32 is in the tilted position, the suction cup system no longer locks the outer housing in position relative to the frame, and the arm axis A and receiving axis Xa form an angle, for example an angle between 5° and 60°, or an angle between 10° and 45°.

The test system 17 may also comprise at least one temperature sensor 35. For example, the temperature sensor 35 is a thermocouple or thermistor.

In an alternative embodiment, the test system may also comprise one or more infrared sensors 35 for contactless measurement of the test container temperature, with a particularly short response time. The infrared sensor(s) can measure both the temperature of the inner surface of the intermediate container 42 and the temperature of the outer surface of the test container 2. More specifically, prior to insertion of the test container into the intermediate container, the infrared sensor(s) can measure the temperature of the inner surface of the intermediate container. After insertion of the test container into the intermediate container 42, the infrared sensor(s) can measure the temperature of the outer surface of the test container. Thus, it is possible to insert the test container once the enclosure formed by the intermediate container has achieved for example a preheating that can simulate a traditional water bath.

As represented in the figures, the test system 17 comprises one or two temperature sensor(s) 35. However, in alternative embodiments, the test system 17 may comprise more than one temperature sensor 35, for example the test system 17 may comprise three temperature sensors which may or may not be similar.

A ventilation device 36 may be provided for rapidly cooling the test container 2. The ventilation device 36 may comprise a ventilator (or fan). Additionally or alternatively, the ventilation device 36 comprises for example one or more ventilation risers. For example, several ventilation risers may be distributed around the receiving container for the purpose of cooling the test container 2 and/or the intermediate container 42. As can be seen in FIG. 6 or FIG. 7, three ventilation risers may be regularly distributed angularly around the receiving container. A ventilation riser extends for example longitudinally for a length substantially equal to the length of the test container 2 and/or of the intermediate container 42. The ventilation riser comprises for example a plurality of air flow openings distributed along its length. Openings may be provided in the receiving container to allow the flow of air from the ventilation device to the test container 2 and/or the intermediate container 42. These openings may be facing the air flow openings of the ventilation riser. The air flow openings may or may not have equal diameters.

Additionally or alternatively, the ventilation device may comprise a ventilator, for example provided inside or outside the outer housing 32 and below the test container 2. The ventilator (or fan) may be associated with Peltier elements in order to obtain faster cooling. The ventilation device/induction assembly further enables precise control of the kinetics of heating and/or cooling the test container 2 (using a controller, for example a PID module).

In such case, as schematically represented in FIG. 11, the test system 17 may comprise a ventilation duct 40 equipped with a fan or ventilator possibly associated with Peltier elements 41. The ventilation duct 40 is for example partly arranged below the test container 2 and is adapted to permit the creation of a cooling channel around the test container. In an alternative embodiment, the fan or ventilator may be arranged directly under the test container without the presence of the ventilation duct 40.

Furthermore, the test system 17 may also comprise a position sensor 37 adapted to detect the position of the arm 18. The position sensor 37 may for example detect a high position of the arm 18 and a low position of the arm 18. For example, in the high position of the arm 18 the first end 21 of the arm 18 is either outside the inner space of the test container 2, or is at a predetermined distance from the meniscus of the content of the test container 2, or is flush with the meniscus of the content of the test container 2. In the low position, the first end 21 of the arm 18 may be positioned against the bottom of the test container 2.

The position sensor 37 may be an optical sensor. In alternative embodiments, the position sensor 37 of the arm 18 may be magnetic and/or mechanical, not optical.

The test system 17 may also comprise a force sensor 38. In particular, the force sensor 38 may be positioned at the support of the electromagnet 27 or close to the electromagnet 27. For example, the force sensor 38 forms the support of the electromagnet 27. The force sensor 38 is adapted to measure the thrust force exerted by the arm 18.

In such case, when performing certain tests, it is possible that after stirring the content of the test container 2 with the arm 18 guided by the guide mechanism 19, the arm 18, which is no longer mechanically connected to the guide mechanism 19, is allowed to "drop" into the test container 2. The arm 18 then begins to descend into the test container 2 due to gravity. The test system 17 as described enables measuring the descent time of the arm 18. During the descent of the arm 18, the content of the test container 2 exerts on the arm 18, wholly or partially immersed in the content, a thrust that is oriented generally vertically upward (in other words, oriented counter to the force of gravity exerted on the arm 18). The force sensor 38 is intended for measuring the thrust force exerted by the content on the arm 18. Thus the force sensor 38 is arranged facing the arm 18. More specifically, the force sensor 38 is arranged facing the first end of the arm 18 and measures the force which is applied to the arm 18 and which is vertically oriented in the second direction. The force sensor 38 may for example be capacitive or piezoelectric or make use of use a strain gauge.

The force sensor 38 is for example adjustable in height relative to the filling opening. Thus, when the rod of the arm 18 rises, the first end 21 of the arm 18 pushes on the force sensor 38 which measures the thrust force.

Similarly, when the rod of the arm 18 descends into the product contained in the test container 2, the force sensor 38 may measure the force of penetration into the product. The force sensor 38 may also measure the retention force exerted by the product on the arm.

The data measured by the force sensor 38 and/or the temperature sensor 35 may be sent to a data processing module and/or a data recording module 39.

In addition, the heating power of the heating device 1 which determines the temperature of the content of the test container 2 and/or the mixing rate of the guide mechanism 19 and/or the stroke amplitude of the guide mechanism 19 can be configured based on the test to be conducted and/or the type of content in the test container 2.

In one possible embodiment of the invention, a processor may be arranged to execute a computer program product implementing data collection operations for data provided by the processing module and originating from the test system 17, as well as to process said data in order to measure or determine the properties of the content of the test container 2 and/or one of the components of the content of the test container 2, for example the first product, in particular a powder. From the collected data and the input parameters for conducting the test on the measurement system, the processor will be able to determine the properties of the tested content, for example the biochemical characteristics of a flour if flour is the tested content. The input parameters for conducting the test may be the heating power of the heating device 1 which determines the temperature of the content of the test container 2 and/or the heating kinetics of the heating device 1. The input parameters may also be the mixing rate of the guide mechanism 19 and/or the stroke amplitude of the guide mechanism 19 and/or the penetration force of the arm 18 into the test container 2 and/or the extraction force of the arm 18 in the test container 2 and/or the thrust force measured by the force sensor 38 as a function of time.

The test system 17 described above may be utilized in a method comprising several steps.

In a preliminary step, which may possibly be performed at a later time, the input parameters of the test and in particular the heating power of the heating device 1 which determines the temperature of the content of the test container 2 and/or the mixing rate of the guide mechanism 19 and/or the stroke amplitude of the guide mechanism 19 are entered.

First, as the test container 2 is outside the intermediate container 42 (and outside the receiving container 3), it is possible to fill the test container 2 with content comprising a first and a second product, the first product being for example a material in powder form and the second product being for example a liquid product. For example, in order to conduct the Falling Number test mentioned above, the test container 2 is filled with content comprising 25 ml of water and 7 grams of flour. In an alternative embodiment, it is possible to add to the test container 2 one or more products other than the two mentioned above. One can then "plug" the test container 2 by the arm to which a plug may be connected in order to close the filling opening of the test container 2. Such a plug may also act as a guide for guiding the rod of the arm 18.

In a second possibly optional step depending on the arrangement of the test system 17, the outer housing 32 of the test system 17 may be tilted relative to the frame 29 so as to expose an insertion opening for the test container 2 in the intermediate container 42 or in the receiving container 3 and therefore in the outer housing 32.

Thirdly, the test container 2 comprising the content and for example with the arm and closed by the plug, is inserted into the intermediate container 42 and therefore into the receiving container 3 and as a result into the outer housing 32.

In a fourth possibly optional step depending on the arrangement of the test system 17, the outer housing 32 of the test system 17 may be tilted with respect to the frame 29, in particular so as to position the test container 2 vertically. More specifically, as the arm 18 is already inserted into the test container 2, the arm 18 axis and the container axis Xr are aligned so that the arm 18 is facing the electromagnet. After tilting, the position of the outer housing 32 relative to the frame 29 is locked.

In a fifth step, the guide mechanism 19 for the arm 18 is operated such that the content of the test container 2 is mixed. After mixing, the first and second products are in solution or in suspension.

In a sixth step, the source of current S is supplied power so that the induction turns 5 receive power. This sixth step may possibly be performed prior to insertion of the test container 2 into the intermediate container 42. The heating of the coil 4 can thus be used to preheat the inner space of the receiving container and more specifically of the intermediate container. The inner space defined by the intermediate container is thus heated. The intermediate container 42 and its inner space Eint are thus heated by induction.

The test container 2 and its content are thus heated by induction and/or heat transfer. The heating temperature of the test container 2 can be controlled using the temperature sensor 35. For example, the equivalent to heating the content of the container in a water bath at 100° C. is performed for the case of the Falling Number test.

The steps of heating the test container 2 and mixing the content of the test container 2 may possibly be reversed. In particular, a preheating step which preheats the inner space of the intermediate container 42 may be performed before insertion of the test container 2 into the intermediate container 42. It is possible to have the temperature sensor 35 signal when the preheating step is achieved. In addition, these steps of heating the test container 2 and mixing the content of the test container 2 may be repeated. The mixing step may possibly be optional.

The heating of the content of the test container 2 by induction and the mixing of the content may take place simultaneously.

It is possible for a control unit to automate the previously mentioned steps. The control unit may for example be coupled to a tilt sensor.

According to the established Falling Number method, the content of the test container 2 is heated to 100° C. throughout the test phase, and after mixing this content by the arm 18, the falling time of the 18 arm in the test container 2 is measured. In the current case, one can measure the time it takes the arm 18 to move from a high position to a low position (where it reaches a predetermined position inside the test container 2). This measurement of the falling time can be achieved by means of the position sensor 37 and a chronometer which is integrated for example into the test system 17.

The falling time can be measured from when stirring begins and during the entire descent phase after the guide mechanism 19 has "released" the arm 18. In other words, the falling time is measured from the high position of the arm, after the arm 18 is uncoupled from the frame 29 and guide mechanism 19 and is only subjected to the force of gravity and slowed by the viscosity of the content.

In this test, it is also possible to measure the thrust force exerted by the content on the arm 18 as previously described.

The test system 17 described also allows the implementation of other tests, including tests on flour quality, and for example continuous stirring (with the arm 18 which is moved by the guide mechanism 19) at a temperature that is constant or is variable according to a law of kinetics of heating.

The test system 17 described also allows setting specific temperature profiles. In particular, the test system 17 allows simply and rapidly varying the temperature of the test container 2 by means of the induction turns 5. The temperature can also be rapidly controlled by the cooler and/or the fan 36.

The invention claimed is:

1. A test system adapted for conducting tests on content, comprising a heating device that comprises: a test container configured for receiving the content, the test container comprising a rigid hollow body defining an inner space and extending longitudinally along a test container axis between a first end and a second end, the second end being closed, the test container comprising an inner surface defining the inner space and an outer surface opposite the inner surface, a receiving container receiving the test container, the receiving container comprising, in a tubular portion of the receiving container, an inner surface oriented towards the outer surface of the test container and an outer surface opposite the inner surface, the inner surface extending longitudinally, parallel to the test container axis, a coil comprising induction turns configured for heating a magnetic material layer surrounding the test container, in order to heat said content that comprises a mixture of a first and a second product, an intermediate container arranged between the inner surface of the receiving container and the test container, the intermediate container including the magnetic material layer and being configured for receiving the test container, and a source of current suitable configured for supplying current to the induction turns, the test system being wherein the induction turns are fixed to the receiving container and extend helically and concentrically around the tubular portion of the receiving container, and wherein the test system further comprises: an arm which is longitudinally inserted in the inner space through an axial opening of the test container, the arm configured for mixing the content of the test container in the inner space during heating of the content by the induction turns, the inner surface defining the inner space being made of a material chosen amongst glass and aluminium, and a guide mechanism configured for guiding the arm within the inner space of the test container along the test container axis, in a first direction and in a second direction that is opposite the first direction.

2. The test system according to claim 1, wherein the intermediate container is suitable for being received in the receiving container, wherein the intermediate container comprises an inner surface oriented towards the outer surface of the test container and an outer surface opposite the inner surface and oriented towards the inner surface of the receiving container.

3. The test system according to claim 2, wherein the intermediate container is made of the magnetic material, the test container being made of aluminium and forming a separating wall between:
   a liquid product included in the mixture of the content; and
   the magnetic material layer formed by the intermediate container.

4. The test system according to claim 2, wherein the intermediate container is fixed in the receiving container, and wherein the test container is movable relative to the intermediate container.

5. The test system according to claim 2, wherein the receiving container comprises a plurality of bosses arranged on the inner face of the receiving container, the plurality of bosses being configured for centering and fixing the intermediate container in the receiving container.

6. A method for implementing a test system according to claim 2, the method comprising the steps of: filling the test container with content comprising the mixture of the first and the second product, placing the test container inside the intermediate container, which is surrounded by the induction turns, mixing the content of the test container with the arm connected to the guide mechanism, by moving the arm along the direction of the test container axis in the first direction and in the second direction, supplying power to the induction turns so as to create induced currents and heat by induction the intermediate container and thus the content of the test container, the intermediate container being made of the magnetic material, wherein the heating of the content by induction and the mixing of the content take place simultaneously.

7. The method according to claim 6, further comprising the steps of: releasing the arm from a retention device so that the arm drops into the test container, measuring the time it takes the arm to drop into the test container.

8. The method according to claim 6, further comprising the steps of:
   providing a temperature sensor,
   monitoring the temperature of the outer surface of the test container.

9. The method according to claim 6, comprising the steps of:
   providing a force sensor,
   measuring a thrust, penetration, and/or retention force exerted by the arm when mixing the content of the test container with the arm and/or after release of the arm by the retention device.

10. The method according to claim 6, wherein the test container, which is aluminium, is in contact with a liquid product only at the inner surface of the test container, the outer surface of the test container being surrounded by the magnetic material of the intermediate container, the receiving container extending annularly to form a tubular wall radially interposed between the induction turns and the intermediate container.

11. The test system according to claim 1, wherein the test container has an insulating handle, wherein the insulating handle is arranged at the first end of the test container.

12. The test system according to claim 1, wherein the receiving container comprises a continuous helical groove extending over the outer surface, and wherein the induction turns of the coil are accommodated in the groove.

13. The test system according to claim 1, wherein the test container comprises an aluminum material.

14. The test system according to claim 1, wherein the arm extends longitudinally along an arm axis between a first end and a second end, the first end being suitable for being arranged in the inner space of the test container, the second end being suitable for being retained outside the inner space of the test container.

15. The test system according to claim 1, wherein the first end of the test container defines a filling opening, and wherein the second end has a draining opening closed by a cap.

16. The test system according to claim 15, wherein the guide mechanism is arranged facing the filling opening and comprises a releasable retention device for the arm, wherein the retention device comprises an electromagnet or a suction cup, and wherein the arm comprises a magnetic element.

17. The test system according to claim 16, further comprising a force sensor configured for measuring a thrust, penetration, or retention force of the arm, wherein: the electromagnet is fixed to the force sensor.

18. The test system according to claim 16, wherein the magnetic element is fixed to the second end of the arm.

19. The test system according to claim 1, further comprising a temperature sensor configured for measuring the temperature of the content of the test container, and wherein the temperature sensor comprises at least one infrared sensor.

20. A test system configured for conducting tests on content, the test system comprising a heating device that comprises: a test container configured for receiving the content, the test container comprising a rigid hollow body defining an inner space and extending longitudinally along a test container axis between a first end and a second end, the second end being closed, the test container comprising an inner surface defining the inner space and an outer surface opposite the inner surface; a receiving container comprising an inner surface oriented towards the outer surface of the test container and an outer surface opposite the inner surface; an intermediate container directly encircling the test container and arranged between the receiving container and the test container; a coil comprising induction turns configured for heating said content that comprises a mixture of a first and a second product via the intermediate container; and a source of current configured for supplying current to the induction turns; wherein: the induction turns are fixed to the receiving container and extend helically and concentrically around the receiving container; the test system further comprises: an arm configured for mixing the content of the test container; and a guide mechanism configured for guiding the arm within the inner space of the test container along the test container axis, in a first direction and in a second direction that is opposite the first direction; the intermediate container is directly received in the receiving container, the intermediate container comprising an inner surface oriented towards the outer surface of the test container and an outer surface opposite the inner surface and oriented towards the inner surface of the receiving container; and in a test configuration, the test container is in contact with a liquid product only at the inner surface of the test container, the outer surface of the test container being surrounded by magnetic material of the intermediate container received in the receiving container.

* * * * *